United States Patent [19]

Kronis et al.

[11] Patent Number: 5,599,792

[45] Date of Patent: Feb. 4, 1997

[54] BONE-STIMULATING, NON-VASOACTIVE PARATHYROID HORMONE VARIANTS

[75] Inventors: K. Anne Kronis, Toronto; Richard P. Bozzato, Etobicoke, both of Canada

[73] Assignee: Allelix Biopharmaceuticals Inc., Mississauga, Canada

[21] Appl. No.: 332,453

[22] Filed: Oct. 31, 1994

Related U.S. Application Data

[63] Continuation of Ser. No. 900,680, Jun. 19, 1992, abandoned.

[51] Int. Cl.$^6$ .................. A61K 38/29; C07K 14/635
[52] U.S. Cl. .................................. 514/12; 530/324
[58] Field of Search ................... 435/69.4; 530/324; 514/12

[56] References Cited

U.S. PATENT DOCUMENTS

| | | | |
|---|---|---|---|
| 4,423,037 | 12/1983 | Rosenblatt et al. | 424/177 |
| 4,698,328 | 10/1987 | Neer et al. | 514/12 |
| 4,968,669 | 11/1990 | Rosenblatt et al. | 514/12 |
| 5,093,233 | 3/1992 | Rosenblatt et al. | 435/7.21 |
| 5,393,869 | 2/1995 | Nakagawa et al. | 530/324 |

FOREIGN PATENT DOCUMENTS

| | | |
|---|---|---|
| 0293159 | 11/1988 | European Pat. Off. . |
| 0357391 | 3/1990 | European Pat. Off. . |
| WO86/06097 | 10/1986 | WIPO . |
| WO88/03165 | 5/1988 | WIPO . |
| WO90/10067 | 9/1990 | WIPO . |

OTHER PUBLICATIONS

Pang et al. Endocrinology (1983) 112(1):284–289.
Rodan et al., *The American Society For Clinical Investigation*, vol. 72, 1983, pp. 1511–1515.
Rabbani et al., *Endocrinology*, vol. 123, No. 6., 1988, pp. 2709–2716.
Kimura et al, *Biochemical and Biophysical Research Communications*, vol. 114, 1983, pp. 493–499.
Keutmann, *Current Research On Calcium Regulating Hormones*, 1987, UTA Press, pp. 57–63.
Fairwell et al, *Biochemistry*, 22:2691 (1983).
Goud et al., *Journal of Bone And Mineral Research*, vol. 6, 1991, pp. 781–789.
Wosnick et al., *Gene*, vol. 76, 1989, pp. 153–160.
Barnett et al., *Nucleic Acids Research*, vol. 18, 1990, p. 3094.
Hendy et al, *Proc. Natl. Acad. Sci.*, vol. 78, 1981, pp. 7365–7369.
Kunkel, *Proc. Natl. Acad. Sci.*, vol. 82, 1985, pp. 488–492.
Higuchi et al, *Nucl. Acids Research*, vol. 16, 1988, pp. 7352–7367.
Rabbani et al., *Biochemistry*, vol. 29, 1990, pp. 10080–10089.
Mok et al., *Endocrine Reviews*, vol. 10, 1989, pp. 420–436.
Daugirdas et al, *Mineral Electrolyte Metab.* vol. 13, 1987, pp. 34–37.

*Primary Examiner*—Marianne P. Allen
*Assistant Examiner*—Karen E. Brown
*Attorney, Agent, or Firm*—Foley & Lardner

[57] ABSTRACT

Described herein are Met$^8$-substituted variants of parathyroid hormone that retain bone stimulating activity yet, unlike their native counterparts, have substantially no vasoactivity. Their production using recombinant DNA-based techniques is also described, as is their therapeutic use, e.g. in the treatment of osteoporosis.

8 Claims, 6 Drawing Sheets

FIG. 2

```
                                      1                                        10
                                      SerValSerGluIleGlnLeu Met HisAsnLeuGlyLysHisLeuAsnSer Met
ompA signal..TCTGTGAGTGAAATACAGCTT ATG CATAACCTGGGAAAACATCTGAACTCG ATG 20                                       30                                       40
GluArgValGluTrpLeuArgLysLysLeuGlnAspValHisAsnPheValAlaAlaLeuGlyAlaAlaProLeuAla
GAGAGAGTAGAATGGCTGCGTAAGAAGCTGCAGGATGTGCACAATTTTGTTGCCCTTGGAGCTGCTCCTCTAGCT 50                                       60
ProArgAspAlaGlySerGlnArgProLysGluAspAsnValLeuValGluSerHisGluLysSer
CCCAGAGATGCTGGTTCCCAGAGGCCCAAAGAAGACAATGTCTTGGTTGAGAGCCATGAAAAAGT 70                                       80
LeuGlyGluAlaAspLysLysAlaAspValAlaAsnValLeuThrLysAlaLysSerGln
CTTGGAGAGGCAGACAAAGCTGATGTGGCTAATGTATTAACTAAAGCTAAATCCCAG...cloning
                                                              site/stop
                                                              codons...
```

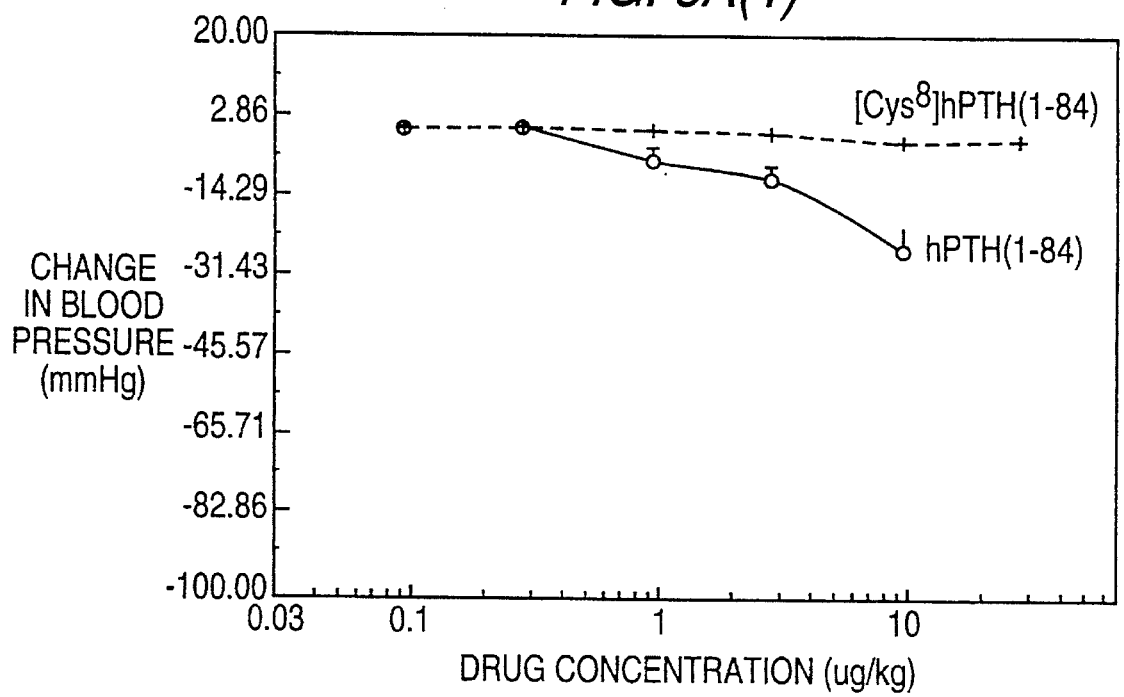
FIG. 3A(1)
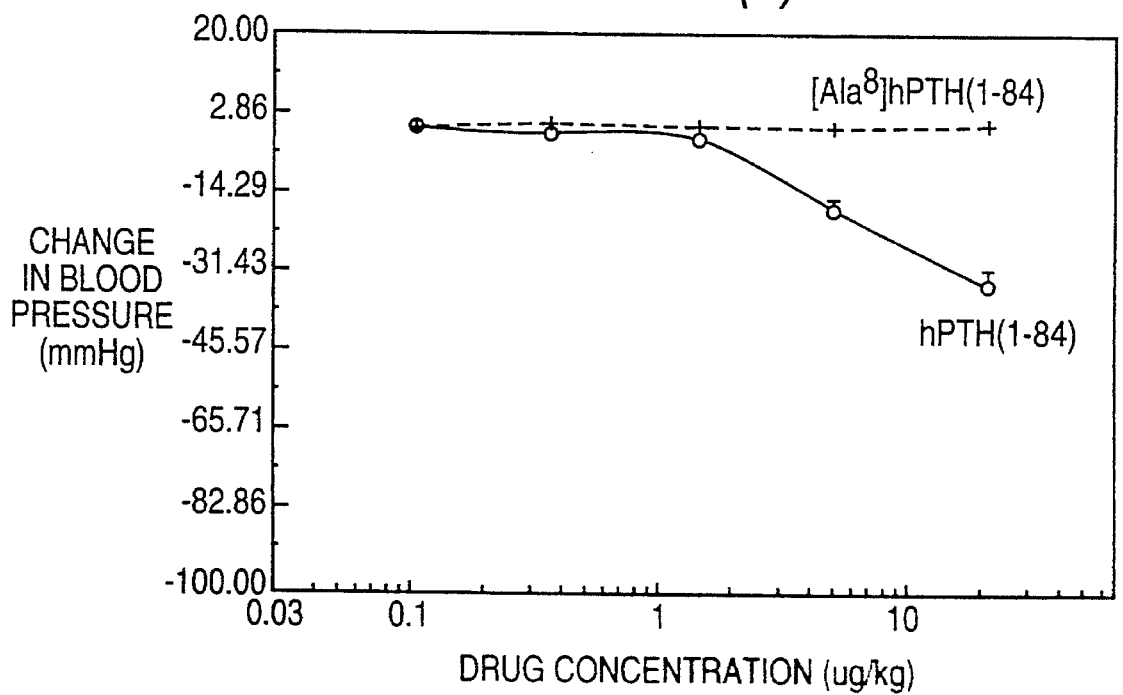
FIG. 3A(3)

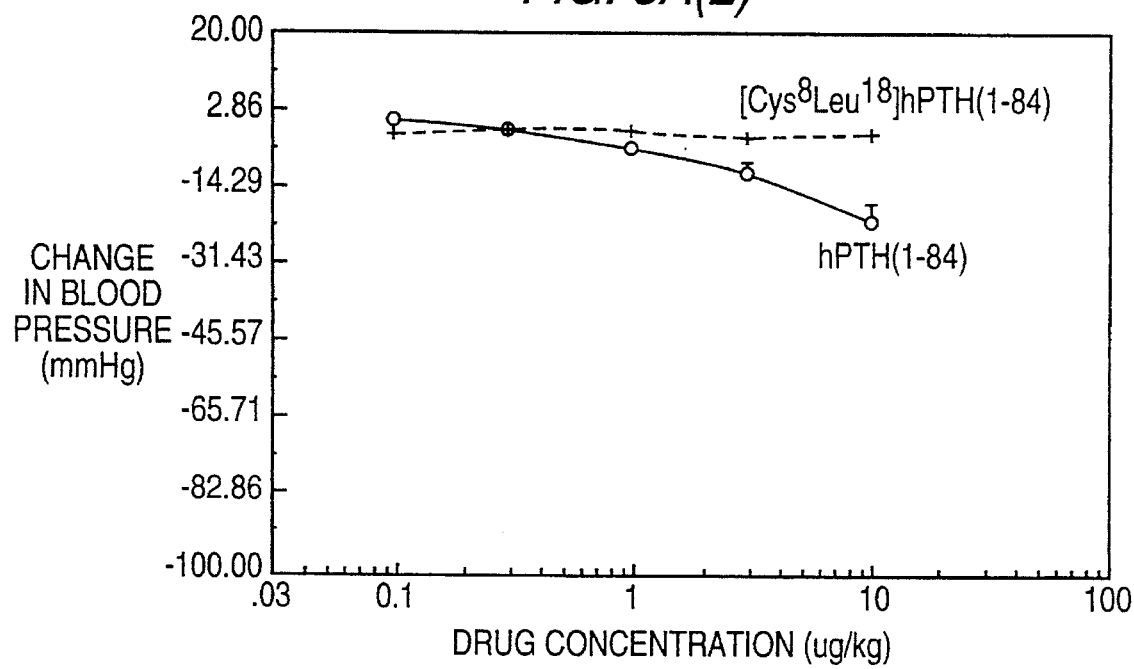
*FIG. 3A(2)*
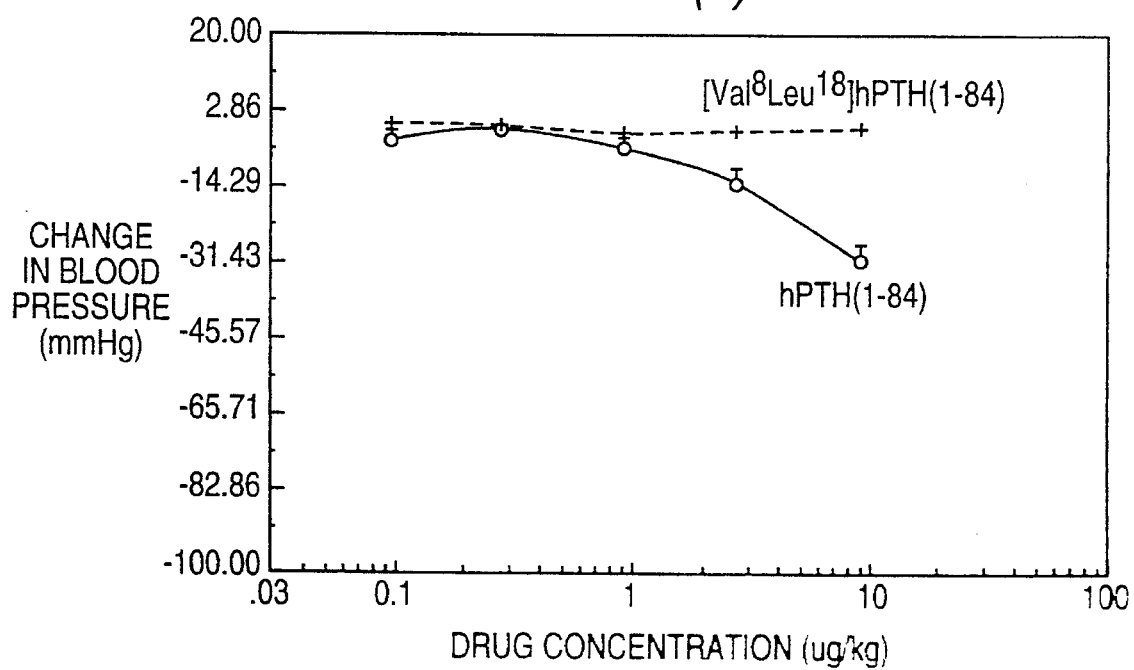
*FIG. 3A(4)*

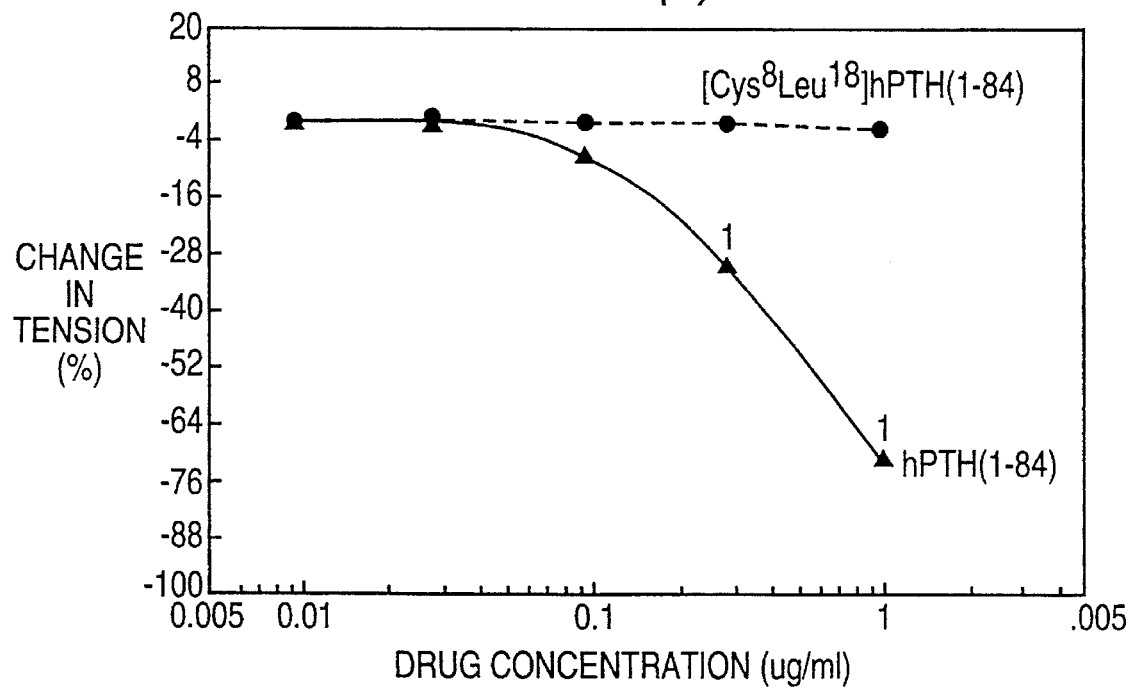
FIG. 3B(1)
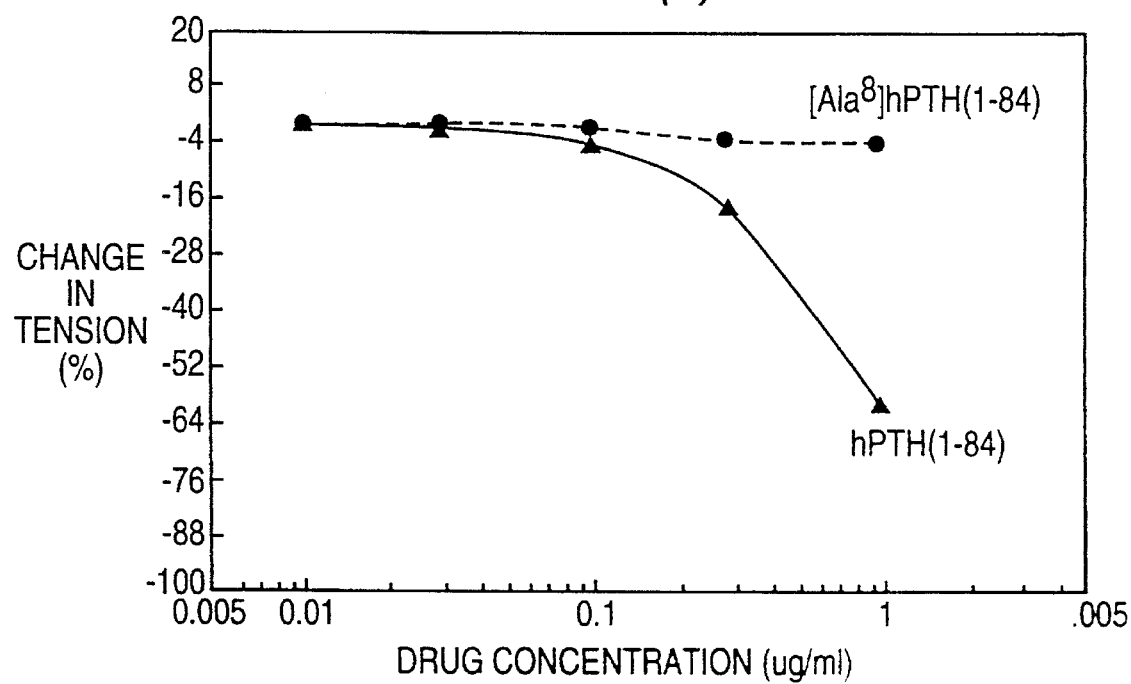
FIG. 3B(3)

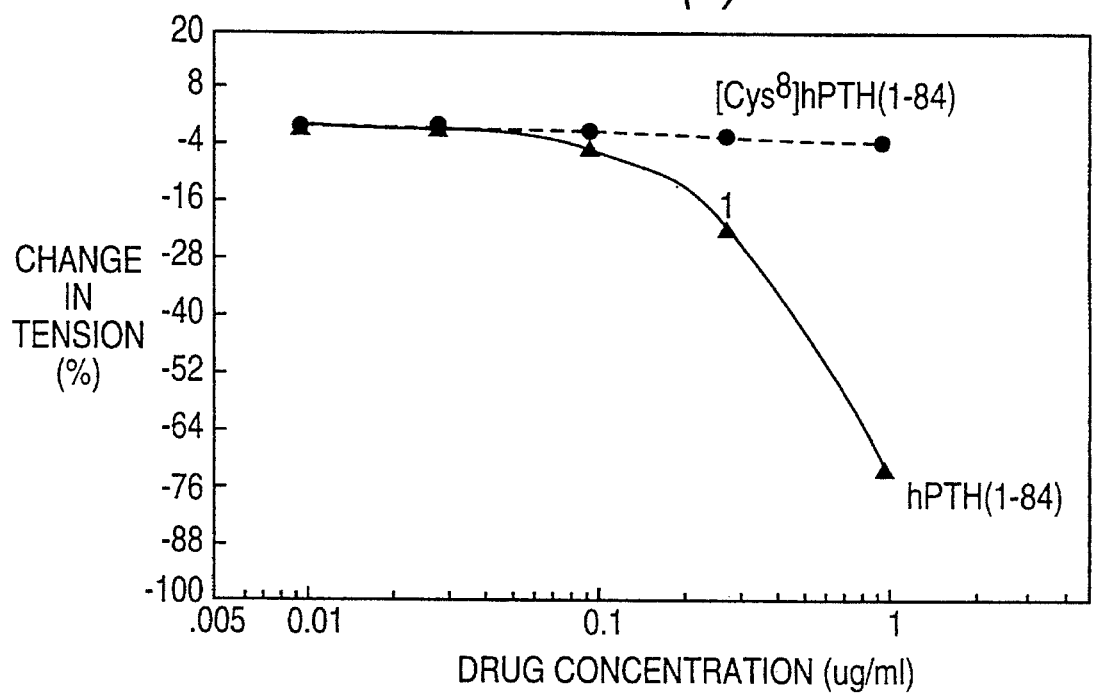
FIG. 3B(2)
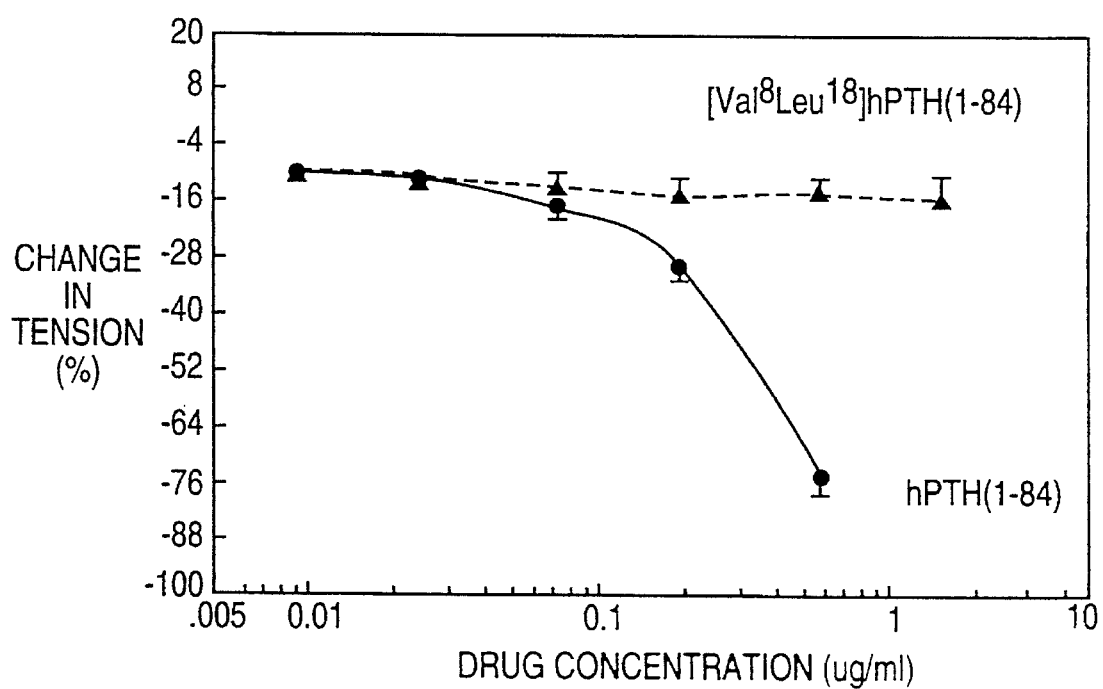
FIG. 3B(4)

BONE-STIMULATING, NON-VASOACTIVE PARATHYROID HORMONE VARIANTS

This application is a continuation of application Ser. No. 07/900,680, filed Jun. 19, 1992, now abn.

FIELD OF THE INVENTION

This invention relates to variants of parathyroid hormone, to the production of such variants particularly via recombinant DNA technology, and to pharmaceutical compositions containing such variants.

BACKGROUND TO THE INVENTION

Parathyroid hormone, or PTH, is a protein product of mammalian parathyroid glands that elicits various biological effects of clinical interest. Of considerable current interest is the role of PTH as a mediator of the physiologically normal, bone remodelling process. In this regard, PTH acts by stimulating bone tissue to modulate skeletal calcium deposit, and thus can mediate an increase in bone mass. It has been suggested that the administration of PTH, or agonistic analogues thereof, would be useful therapeutically to treat and/or prevent bone-related disorders, such as osteoporosis. It has also been revealed that PTH is a vasoactive protein, and exerts a vasorelaxant effect on the cardiovascular system, and may be useful in controlling systemic blood pressure (see for example the article by Tenner et al in Vascular Neuroeffector Mechanisms, 4th International Symposium, Raven Press, 1983, pp289–293; and see the review by Mok et al, Endocrine Reviews, 1989, 10(4):420).

To further the development of PTH as a bone therapeutic, it would be desirable to reduce its cardiovascular action, particularly so that repeated administration during treatment, for example of an osteoporotic patient, does not contribute to an altered cardiovascular state. Accordingly, it is a general object of the present invention to provide novel variants of parathyroid hormone that exhibit bone stimulating activity and reduced vasoactivity.

It is another object of the present invention to provide variants of parathyroid hormone having substantial bone stimulating activity and reduced vasoactivity, which are amenable to production by recombinant DNA technology.

It is also an object of the present invention to provide a pharmaceutically useful composition containing a novel parathyroid hormone variant that exhibits bone stimulating activity and reduced vasoactivity.

It is another object of the present invention to provide a method for treating patients afflicted with an osteopenic condition, such as osteoporosis.

SUMMARY OF THE INVENTION

It has now been found that the vasorelaxant activity of parathyroid hormone can be reduced significantly without substantially affecting the bone stimulating activity thereof, by replacing the methionine resident at position 8 in the hormone with an amino acid selected from alanine, valine and cysteine. More particularly, and according to one aspect of the present invention, there is provided a bone-stimulating, substantially non-vasoactive compound, of the formula:

[X$^8$]PTH wherein:

X represents a Met$^8$-replacement amino acid selected from among the group consisting of cysteine, valine and alanine; and PTH represents a bone stimulating, Met$^8$-containing compound selected from a mammalian parathyroid hormone, a fragment of said hormone, a variant of said hormone, and a fragment of said variant.

In preferred embodiments of the invention, the replacement amino acids are incorporated into human PTH or into a Met$^8$-containing, bone-stimulating fragment or variant of human PTH.

According to another aspect, the PTH variants of the present invention consist essentially of genetically encoded amino acids and are produced by application of recombinant DNA techniques. Accordingly, there is provided a cellular host having incorporated expressibly therein a DNA molecule which codes for a PTH variant of the present invention. In a related aspect of the present invention, there is provided a method for producing a PTH variant having bone stimulating activity and reduced vasoactivity, comprising the step of culturing a cellular host in which DNA coding for the PTH variant is expressibly incorporated.

The PTH variants of the present invention are suitably employed as therapeutics for the treatment of bone disorders, such as osteoporosis. According to another aspect of the present invention, therefore, there is provided a pharmaceutical composition comprising a pharmaceutically acceptable carrier and a PTH variant of the present invention.

These and other aspects of the invention are now described in greater detail and with reference to the accompanying drawings, in which:

BRIEF REFERENCE TO THE DRAWINGS

FIG. 1 is a map of plasmid pX in which DNA coding for human PTH is linked operably with DNA enabling expression thereof in *E. coli*;

FIG. 2 provides the nucleotide sequence (SEQ ID NO:1) of the human PTH-encoding region of the plasmid shown in FIG. 1, and also provides for reference the amino acid sequence of human PTH. Methionine residues at positions 8 and 18 are highlighted using boxes; and FIGS. 3A and 3B illustrate graphically the relative vasoactivities of human PTH and human PTH variants.

DETAILED DESCRIPTION OF THE INVENTION AND ITS PREFERRED EMBODIMENTS

Figure 1:
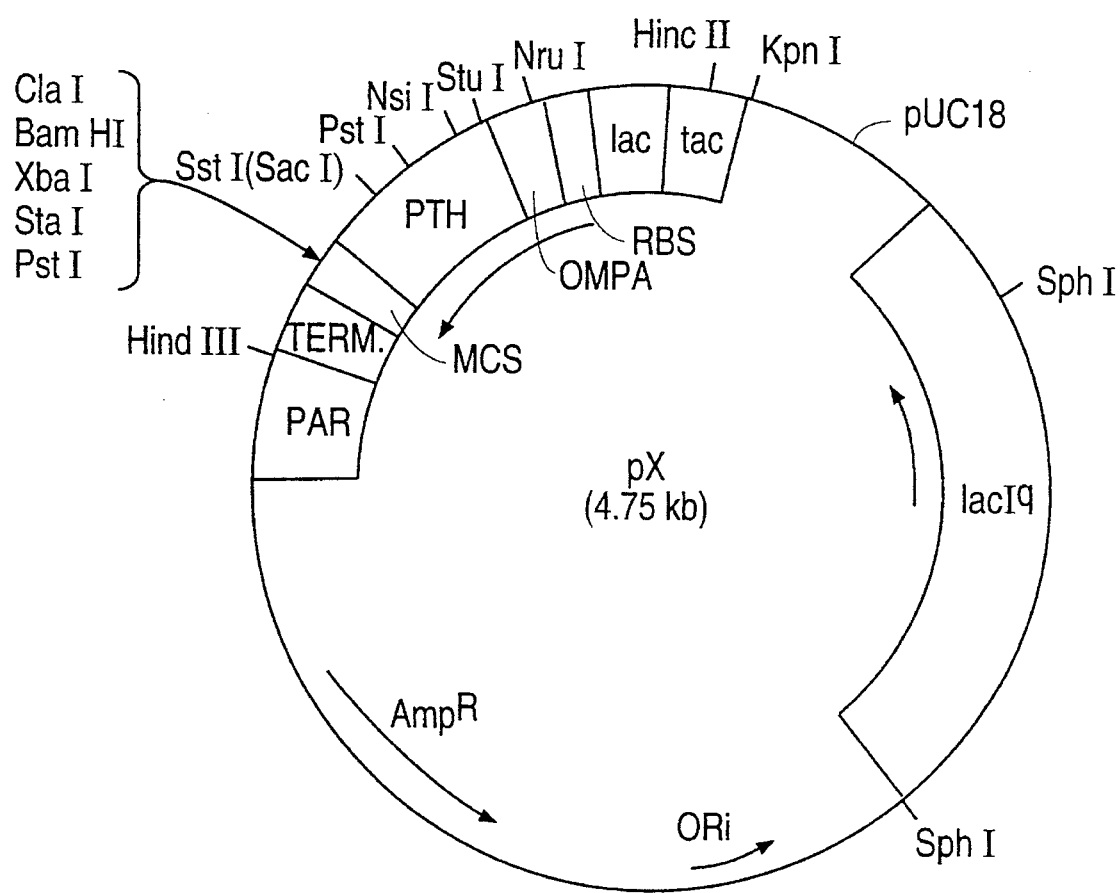

The present invention relates to PTH variants that exhibit both bone stimulating activity and reduced vasoactivity.

In the present specification, "bone stimulating activity" is defined in the context of the osetosarcoma-based adenylate cyclase assay employed conventionally in the art. Briefly, this assay provides an in vitro determination of the extent to which PTH stimulates adenylate cyclase activity in rat osteosarcoma cells of the 'UMR' lineage, and thus provides an indication of PTH effects on bone tissue in vivo. Protocols for conducting the assay have been described by Rodan et al, 1983, J. Clin. Invest., 72:1511 (in which the osteosaracoma cells of the ROS lineage are employed) and by Rabbani et al, 1988, Endocrinol., 123:2709 (which employs the line UMR-106). PTH variants that exhibit, in the UMR-based assay, an EC$_{50}$ of at least 2,000 nM i.e. 2,000 nM or lower, are herein characterized as having "bone stimulating" activity.

In addition to retaining bone stimulating activity, the PTH variants of the present invention are particularly characterized by "reduced" vasoactivity, i.e. a vasorelaxant activity that is reduced, relative to native (Met⁸-containing) human PTH. In the present specification, vasorelaxant activity is defined according to effects on rat blood pressure, and in the context of the in vitro, helical strip assay described by Daugirdas et al in Mineral Electrolyte Metab., 1987, 13:33, which measures PTH-induced relaxation of an arginine-vasopressin-contracted helical strip taken from rat tail vein. PTH variants having no statistically significant effect on one or both of blood pressure and helical strip relaxation are herein characterized as having a "reduced vasorelaxant activity".

The PTH variants of the present invention conform to the general formula:

[X⁸]PTH     (1)

wherein X is a Met⁸-replacement amino acid selected from cysteine, alanine and valine, and "PTH" represents a bone stimulating, Met⁸-containing compound selected from a mammalian parathyroid hormone, a fragment of said hormone, a variant of said hormone comprising from 1 to 5 amino acid replacements, and a fragment of said variant. In the above formula, the numeral identifies the location of the amino acid X within the PTH molecule, relative to the N-terminal amino acid thereof. For consistency and as is conventional in the art, X is assigned the same positional number when present in the context of N-terminally truncated or extended forms of PTH, such as analogues or fragments of PTH.

In one embodiment of the invention, "PTH" in the above formula refers to a Met⁸-containing form of mammalian PTH selected from human PTH, bovine PTH, rat PTH and porcine PTH. The term "human PTH" refers to the mature form of the hormone, which consists of 84 amino acids arranged in the sequence reported by Kimura et al, 1983, Biochem. Biophys. Res. Comm., 114(2):493. The terms "human PTH", "hPTH" and "hPTH(1–84)" are used interchangeably herein. The terms "bovine PTH", "rat PTH" and "porcine PTH" refer also to the mature form of the hormone, each of which consists of 84 amino acids arranged in the sequences reported by Keutmann et al in Current Research on Calcium Regulating Hormones, Cooper, C. W.(Ed.), 1987, University of Texas Press, Austin, pp.57–63. In particular embodiments of the present invention in which the replacement amino acid is incorporated within human PTH, specific compounds of formula (1) include [Cys⁸] hPTH(1–84), [Ala⁸]hPTH(1–84)and [Val⁸]hPTH(1–84), and bovine counterparts thereof.

According to another embodiment of the present invention, "PTH" in the above formula refers to a bone stimulating fragment of a Met⁸-containing form of a mammalian PTH selected from human PTH, bovine PTH and porcine PTH. Thus, for example, the replacement amino acids may be incorporated into bone stimulating fragments of mammalian PTH that comprise at least the first 27 residues of the mammalian PTH, and usually not more than about the first 38 residues of the mammalian PTH. In one embodiment of the invention, a selected replacement amino acid is introduced into a bone stimulating mammalian PTH fragment that comprises the first 34 residues of the mammalian PTH. In specific embodiments of the present invention, compounds of formula (I) include [Cys⁸]hPTH(1–34), [Ala⁸] hPTH(1–34) and [Val⁸]hPTH(1–34) and bovine counterparts thereof.

According to another embodiment of the present invention, "PTH" in the above formula refers to a bone-stimulating variant of a Met⁸-containing form of mammalian PTH or a bone stimulating fragment thereof, which variant harbours one or more, usually not more than about 5, amino acid substitutions within the mammalian PTH sequence but at site(s) other than Met8. Thus, for example, a selected replacement amino acid can be introduced into such bone stimulating PTH variants as; mammalian PTH and fragments thereof in which the methionine resident at position 18 is replaced by cysteine or an oxidation-resistant amino acid, preferably a hydrophobic amino acid such as leucine, norleucine, isoleucine, valine and alanine (see co-pending U.S. Ser. No. 07/806,271 filed Dec. 13, 1991); mammalian PTH and fragments thereof in which one or more, preferably all, of the residues Arg²⁵Lys²⁶Lys²⁷ are replaced by a trypsin-insensitive amino acid such as histidine, glutamine, asparagine and leucine or other hydrophobic amino acid (see co-pending U.S. Ser. No. 07/863,014 filed Apr. 3, 1992); mammalian PTH and fragments thereof in which glycine at position 12 is replaced by alanine, D-alanine, isobutyric acid, proline, tryptophan or asparagine (see Wingender et al, WO90/10067 and Rosenblatt et al, U.S. Pat. No. 4,968,669); mammalian PTH and fragments in which tryptophan at position 23 is replaced by leucine, N-methylphenylalanine or D-tryptophan (see Merck & Co., EP 293,159); mammalian PTH and fragments in which histidine at position 32 is replaced by arginine, leucine, lysine or serine (see Wingender et al, supra); and mammalian PTH and fragments thereof in which phenylalanine at position 34 is replaced by tyrosine. In specific embodiments of the invention, compounds of formula (I) include [Cys⁸Leu¹⁸]hPTH and [Val⁸Leu¹⁸]hpTH, as well has bone stimulating fragments thereof, and bovine equivalents thereof.

According to one aspect of the present invention, the PTH variants may be produced either by chemical synthesis or using recombinant DNA-based production techniques. For chemical synthesis, the solid phase peptide synthesis technique has been successfully applied in the production of human PTH and can be used for the production of the PTH variants of the present invention (for guidance, see Kimura et al, supra, and see Fairwell et al, Biochem., 1983, 22:2691). Success with producing human PTH on a relatively large scale has been reported by Goud et al in J. Bone Min. Res., 1991, 6(8):781, incorporated herein by reference. This production approach generally entails the use of automated synthesizers and appropriate resin as solid phase, to which is attached the C-terminal amino acid of the desired PTH variant. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques. Such procedures are generally described in numerous publications and reference may be made, for example, to Stewart and Young, *Solid Phase Peptide Synthesis*, 2nd Edition, 1984, Pierce Chemical Company, Rockford, Ill.

More desirably, and in accordance with one aspect of the present invention, the PTH variants consist essentially of genetically encoded amino acids, and are produced by culturing a cellular host in which DNA coding for the desired PTH variant is expressibly incorporated. Incorporation of the desired DNA, in expressible form, can be achieved using the now conventional recombinant DNA-based approach, wherein DNA coding for the PTH variant is linked operably with DNA enabling expression of the PTH variant-encoding DNA, to form a recombinant DNA expression construct which is then introduced into the selected cellular host by DNA-mediated transformation, electroporation or the like. A cellular host having DNA coding for a PTH variant incorporated "expressibly" therein is characterized by the ability to yield the desired expression product, when cultured appropriately. A cellular host having DNA coding for a PTH variant incorporated "stably" is able to retain such DNA during culturing, and to transmit such DNA to its progeny through at least several generations. For eukaryotic cellular hosts, such stability is typically conferred by genomic integration of the PTH variant-encoding DNA. In bacteria, which typically harbour transforming DNA in the form of autonomously replicating plasmids, such stability is usually ensured by culturing a strain carrying plasmid-conferred antibotic resistance in the presence of the antibiotic.

For expression in the cellular host, DNA coding for a selected PTH variant may be obtained using techniques that are well established in the art. For example, a DNA sequence coding for a given PTH variant may be synthesized de novo in accordance with methods standard in the gene synthesis art. Briefly, this entails the successive 3' to 5' coupling of suitably protected nucleotide reagents in an automated synthesizer such as the Applied Biosystems Inc. model 380B DNA synthesizer, and then the recovery by gel purification of the deprotected polynucleotide. The block ligation approach may be employed, whereby "blocks" of oligonucleotide pairs, up to about 80 nucleotides in length, are prepared and ligated in correct succession by overhang complementarity, as described for example by Wosnick et al in Gene, 1989, 76:153. In an alternative approach, the desired DNA may be synthesized in toto, and then amplified by polymerase chain reaction (PCR), using the approach described by Barnett et al in Nucl. Acids Res., 1990, 18(10):3094.

It will be appreciated that alternative strategies may also be applied to generate DNA coding for the desired PTH variant. For instance, DNA coding for human PTH may be obtained and then used as a template e.g. mutagenized site-specifically, to introduce the desired amino acid change at the genetic level. DNA coding for human PTH may be obtained from an appropriate human cDNA library, from a commercial source or by de novo synthesis according to the procedures outlined above, and in accordance with the PTH-encoding nucleotide sequence reported for example by Hendy et al, Proc. Natl. Acad. Sci. USA, 1981, 78:7365, incorporated herein by reference, or a PTH-encoding equivalent thereof. The PTH-encoding DNA template may be converted to DNA coding for a PTH variant using the well established oligonucleotide-directed mutagenesis technique, as generally described for example by Kunkel et al, 1985, Proc. Natl. Acad. Sci. USA, 82:488. This technique is conveniently accomplished with high efficiency using the *E. coli* based system for synthesis and propogation of the altered gene in an appropriate vector, such as M13top 18. Kits useful for performing such procedures in vitro are available commercially. Also suitable for obtaining PTH variant-encoding DNA from a PTH-encoding template is the related, technique in which site-directed mutagenesis is achieved using a polymerase chain reaction (PCR)-based approach. One variant of this method, termed "recombinant PCR" is described by Higuchi et al, Nucl. Acids. Res., 1988, 16:7351.

Once obtained, DNA coding for the desired PTH variant is incorporated stably and expressibly into a cellular host selected to serve in production of the PTH variant. A variety of organisms are suitable as hosts for production of the PTH variants. These include eukaryotic hosts including yeasts such as Saccharomyces, Pichia and Kluveromyces, filamentous fungus hosts including Aspergillus species such as *nidulans, niger* (or *awamoni*) and *oryzae,* insect cell hosts, and mammalian cell hosts including the CHO and COS cell lines. The PTH variants are not dependent on glycosylation for activity, and thus can suitably be produced in bacterial hosts including Streptomyces, Bacillus and, preferably, in *E. coli*. Recombinant DNA expression systems and culturing media/protocols enabling production in these hosts of a desired protein have already been established, and these systems may be employed in the conventional manner for the specific purpose of producing PTH variants. *E. coli* production of PTH variants may be achieved, for example, using expression systems based on the lac promoter (see Rabbani et al, Biochem., 1990, 29:10080) and expression/ secretion systems based on the tac promoter (see Wong et al, EP 357,391 ). Yeast expression may be achieved using expression systems based for example on the expression controlling regions of the alpha-1 mating factor gene as described by Gautvik et al in WO88/03165. Production in Aspergillus may be achieved using secretion systems based on expression controlling regions of the *A. nidulans alcA* gene or the *A. niger* glucoamylase gene, as described for example by Gwynne et al in WO86/06097.

The PTH variant produced upon culturing of the production host is extracted and purified using techniques that are also established in the art. In general, the human PTH variants have characteristics that are similar generically to those exhibited by human PTH, and may therefore be extracted and purified in substantially the same manner. Like PTH, the variants have a net positive charge at neutral pH (pI of about 9.3) and can be purified therefore by ion exchange chromatography, e.g. using cation exchange columns. The PTH variants are also, like PTH, hydrophobic in nature, and may therefore be purified by hydrophobic interaction chromatography e.g. on columns packed with a phenyl-Sepharose matrix. Also, of course, molecular sieves may be used to separate PTH variants from other proteins unrelated by size, and affinity columns may be employed which comprise PTH affinity agents such as hydroxyapatite or PTH antibody. Preferably, purification of the PTH variant is achieved by applying the protein mixture, optionally supplemented with an anti-oxidant such as β-mercaptoethanol or cysteine, to a cation exchange column e.g. S-Sepharose, and then applying the eluted retentate to a column having a hydrophobic matrix e.g. a column having a phenyl, octyl or butyl side chain such as phenyl-Sepharose, phenyl-Superose, octyl-Sepharose or butyl 650M. The retentate eluted from the hydrophobic matrix, or material purified by any suitable alternative procedure, is then suitably subjected to a final purification step using reversed phase high performance liquid chromatography (HPLC) using, for example, an acetontrile/water system and an ion-pairing agent such as trifluoroacetic acid, heptafluorobutyric acid or, more desirably, a cationic agent such as triethylamine salt, e.g. phosphate.

For therapeutic use, a PTH variant is desirably purified to the extent that it migrates as a single peak on reversed phase HPLC, and exhibits a single band on polyacrylamide gel electrophoresis in the presence of SDS. Once purified, the PTH variant may be formulated to provide pharmaceutical compositions especially suited for treating patients afflicted with an osteopenic state. Compositions containing PTH variant may, for example, be delivered systemically to treat bone disorders such as osteoporosis and for this purpose is suitably formulated either as injectables or ingestibles or for nasal insufflation. Sterile injectable compositions are preferred, and will generally comprise an effective dose of the PTH variant, in admixture with normal saline and suitable solubilizing agent e.g. dilute acetic acid.

The dose of PTH variant effective to treat a given bone condition will depend of course on the nature and severity of the condition, and on such other factors as are normally considered and evaluated in clinical trials and by the attending physician. For treating osteoporosis, the PTH variant is administred in amounts large enough to stimulate bone remodelling, but not so large as to cause net bone resorption or sustained increase in serum calcium levels. Reference may be made to U.S. Pat. No. 4,698,328 for guidance on the administration of PTH to treat osteoporosis. Using the effective PTH doses in a given clinical situation for guidance, the dose of PTH variant required to elicit a similar effect can be calculated based on the relative activity of the PTH variant, as noted in the table herein. It is anticipated that an effective dose of PTH variant of the present invention will generally be in the range from about 1 µg/kg to about 100 mg/kg, such as from about 100 µg/kg to about 10 mg/kg.

Like PTH, the PTH variants may be administered in combination with other agents useful in treating a given clinical condition. When treating osteoporosis and other bone-related disorders for example, the PTH variants may be administered in conjunction with a dietary calcium supplement or with a vitamin D analogue (see U.S. Pat. No. 4,698,328). Alternatively, the PTH variant may be administered, preferably using a cyclic therapeutic regimen, in combination with bisphosphonates, as described for example in U.S. Pat. No. 4,761,406, or in combination with one or more bone therapeutic agents such as calcitonin and estrogen.

EXAMPLES

The examples which follow describe production of PTH and PTH variants. Production of these proteins was achieved using, as a matter of convenience only, an *E. coli* based system substantially as described by Wong and Sutherland in European patent application 89308753.6 (published as EP357,391 on 7 March 1990), the contents of which are incorporated herein by reference. This system makes use of the commonly available *E. coli* JM101 strain as host and employs as vector a pUC18 derivative, designated pX. As is shown in FIG. 1, pX incorporates the par element of pSC101 to enhance frequency of plasmid transmission, the lacIq gene of pMMB22 to enable overproduction of the lac repressor, and a PTH-excretion cassette. Incorporated in the excretion cassette is human PTH-encoding DNA that was synthesized using the block ligation technique reported by Wosnick et al, supra, and in accordance with the PTH-encoding nucleotide sequence reported by Hendy et al, supra. Fused 5' of, and precisely to, the PTH-encoding DNA is the signal sequence of the *E. coli* ompA gene, which is capable of directing the PTH portion of the expression product across the host inner membrane, and ultimately to the culturing medium. For regulated expression of the coding region, the plasmid operably incorporates the tac promoter, the lac operator and a consensus ribosomal binding site. Transcriptional termination is controlled by the *E. coli* trpA gene terminator, and translational stop codons are provided in all three reading frames, immediately 3' of the PTH-encoding DNA.

Thus, the pX expression vector, used for the production of human PTH and PTH variants, is substantially the same as that described by Wong and Sutherland, supra, except that the multiple cloning site downstream of the PTH gene contains cleavage sites for the restriction enzymes ClaI, BamHI, XbaI, StuI and PstI, in the order indicated on FIG. 1. The precise nucleotide sequence of the PTH-encoding region of the excretion cassette is illustrated in FIG. 2.

Example 1—Production of Human PTH(1–84)

Plasmid pX was transformed into competent *E. coli* JM101 using standard procedures. Positive transformants were identified following growth overnight at 30° C. on plates containing 2YT/agar and 70µg/ml ampicillin. PTH-producing transformants were then examined for PTH activity, following growth and induction in shake flasks, by IRMA analysis of conditioned medium, and frozen stocks of the selected transformants were subsequently prepared by mixing an equal volume of the shake flask culture at the mid-log growth phase with sterile glycerol to yield 50%(v/v) glycerol stocks. These stocks were subsequently stored at −80° C. When needed, transformants were recovered from the frozen stock by scraping, and were then streaked on ampicillin-containing plates of 2YT/agar.

To produce human PTH, freshly plated transformants were picked as single colonies and then inoculated into 50 ml Erlenmeyer flasks containing 15 ml of a liquid medium which contained 2YT, glucose and ampicillin in the standard mixture. Following overnight growth with shaking at 30° C., the cultures were diluted 20-fold with fresh medium, and then grown for three hours at 30° C. with shaking. Expression of the PTH-encoding DNA was then de-repressed by addition of 1.0 mM IPTG. After growth for four hours in the presence of IPTG, the culture was cooled to 4° C. and centrifuged. The supernatant was then harvested and human PTH contained therein was recovered and assayed for PTH activity.

To obtain greater quantities of human PTH(1–84) and the PTH variants for purification and bioassay, larger volumes of conditioned media were collected. In particular, freshly plated transformants were picked as single colonies and then inoculated into 500 ml flasks containing 200 ml of the medium described above. Following overnight growth with shaking at 30° C., the cultures were inoculated into 2 L bioreactors containing 1.5 L of the liquid medium, and then grown for 5 hours at 30° C. with stirring. Expression of the PTH- or PTH variant-encoding DNA was then induced by addition of 1.0 mM IPTG. After growth for about 8 hours in the presence of IPTG, the culture was cooled to 4° C. and centrifuged. The supernatant was then harvested, and the PTH or PTH variant contained therein was purified in the manner described in Example 6.

The examples which follow describe production of PTH variants. To obtain DNA coding for these variants, the in vitro site-directed mutagenesis technique described by Kunkel et al, supra was applied. To perform this procedure there was first obtained plasmid RX which is an M13 mp18-based plasmid lacking a functional tac promoter. Plasmid RX thus served as the template for conducting mutagenesis on the PTH-encoding DNA, in order to generate DNA coding for a desired PTH variant. The particular mutagenesis strategy is described in the examples below.

Example 2—Production of a [Cys$^8$] Variant of PTH

To provide DNA coding for a PTH variant in which Met$^8$ is replaced by cysteine, plasmid RX was first recovered in single stranded form and about 1 µg thereof was incubated, at 85° C. in Hin buffer, with about 100 ng of a mutagenic oligonucleotide capable of hybridizing specifically to that region of the PTH gene containing the Met$^8$ codon. The specific sequence of the oligonucleotide, designated M4, is shown below where underlining indicates the codon change relative to the PTH-encoding template:

M4 oligo:(SEQ ID NO: 6)5' CCAGGTTATG
GCAAAGCTGTATTTCAC 3'

After slow cooling, the annealed fragment was treated with DNA polymerase 1(Klenow) in the presence of all four dNTPs, for about 2 hours at 37° C. and then for 4 hours at room temperature, in order to form the full length double-stranded plasmid, designated pRXM4. Competent host JM101 was then transformed by pRXM4, and plaques were screened by restriction digest analysis and by DNA sequencing to select those carrying the desired mutation.

pRXM4 is then digested with NruI and XbaI and the resulting small fragment is isolated by low melting point agarose. Plasmid pX is similarly digested, and the large NruI/XbaI fragment is isolated. The relevant isolated fragments are then ligated, to form plasmid pXM4, which carries DNA coding for [Cys$^8$]hPTH. This was confirmed by restriction digest analysis and DNA sequencing.

Competent *E. coli* JM101 was transformed with pXM4 and the transformants were then selected in accordance with the procedures outlined in Example 1. Supernatant containing the [Cys$^8$]PTH for subsequent purification was then obtained by culturing the pXM4 transformant, as described in example 1.

Example 3—Production of an [Ala$^8$] Variant of PTH

In a manner similar to that described in Example 2, there was obtained DNA coding for a human PTH variant in which the Met$^8$ codon was replaced by an alanine codon, In particular, the Met$^8$ codon in pRX was replaced site-specifically using an oligonucleotide having the sequence shown below, where underlining identifies the introduced codon change:

M3 oligo:(SEQ. ID NO:5' CCAGGTTATG
AGCAAGCTGTATTTCAC 3'

This generated plasmid pRXM3, the small NruI/XbaI fragment of which is ligated to the large NruI/XbaI fragment of pX to yield pXM3. *E. coli* JM101 was then transformed with pXM3 and the transformants were cultured to provide supernatants containing [Ala$^8$]hPTH, in the manner described in Example 1.

Example 4—Production of a [Cys$^8$Leu$^{18}$] Variant of PTH

In a manner similar to that described in Example 2, there was obtained DNA coding for a human PTH variant in which Met$^8$ is replaced by cysteine and Met$^{18}$ is replaced by leucine. This was achieved by incubating pRXM4, which already bears the Cys$^8$ codon, with an oligonucleotide of the sequence (SEQ. ID 3) CTCTCTCCAGCGAGTTC which introduces the Leu$^{18}$ codon (underlined), to yield plasmid pRXC3. Following sequencing which confirmed incorporation of the Cys$^8$ and Leu$^{18}$ codons, the NruI/XbaI fragment was cloned as described in example 2, and the resulting plasmid was transformed into *E. coli* JM101. Transformants were selected, the selected transformants were grown in shake flasks, and the shake flask supernatants containing [Cys$^8$Leu$^{18}$]hpTH were recovered and stored frozen for subsequent analysis, all in accordance with the methods described in Example 1.

Example 5—Production of a [Val$^8$Leu$^{18}$] Variant of PTH

In a manner similar to that described in Example 4, there was obtained DNA coding for a human PTH variant in which Met$^8$ is replaced by valine and Met$^{18}$ is replaced by leucine. This is achieved by incubating pRXC3 (example 4), which already bears the Leu$^{18}$ codon, with an oligonucleotide of the sequence (SEQ. ID NO:4) CCAGGTTATGAAC AAGCTGTATTTCAC which replaces the Cys$^8$ codon with a Val$^8$ codon (underlined), to yield plasmid pRXS326. Following sequencing which confirmed incorporation of the Val$^8$ and Leu$^{18}$ codons, the NruI/XbaI fragment was cloned as described in example 2, and the resulting plasmid was transformed into *E. coli* JM101. Transformants were selected, the selected transformants were grown in shake flasks, and the shake flask supernatants containing [Val$^8$Leu$^{18}$]hPTH were recovered and stored frozen for subsequent analysis, all in accordance with the methods described in Example 1.

*E. coli* transformants were obtained and cultured, and supernatants containing the variant were collected individually as described in example 1, for analysis as now described in example 6.

Example 6—Purification and Evaluation of PTH and PTH Variants

The conditioned medium collected from the transformants of Examples 1–5 was, in each case, adjusted to about pH 4 with glacial acetic acid. In some but not all cases, mercaptoethanol was then added to a final concentration of 10 mM and the solution was centrifuged. The supernatant was harvested and then passed through a column containing the cation exchange resin S-Sepharose FastFlow (Pharmacia, bed volume 50 ml) pre-equilibrated with 0.04 M ammonium acetate/10 mM β-mercaptoethanol (pH4.0). PTH or the PTH variant, bound to the resin, was eluted by applying a concentration gradient of ammonium acetate as eluant of from 0.04 M–1.0 M ammonium acetate/10 mM β-mercaptoethanol (pH4.0). PTH or the PTH variant eluted from the resin at about 0.6 M ammonium acetate. Eluant fractions, containing PTH or the PTH variant (as measured by the Allegro two-site IRMA purchased form Joldan Diagnostics, California, catalogue #40-2170, or by absorbance at 280 nm), were combined to provide PTH or the PTH variant at about 60–70% purity.

Samples of greater purity were obtained by subjecting the combined fractions to a chromatographic separation using the resin phenyl-Sepharose FastFlow (Pharmacia). More particularly, the pH of the combined S-Sepharose fractions was adjusted to pH 8 with 5N NaOH. This solution was then applied to a column containing phenyl-Sepharose (6 ml bed volume), pre-equilibrated with the buffer (6 volumes of 1.0M ammonium acetate (pH4.0) and 4 volumes of 40 mM ammonium acetate (pH4.0), then adjusted to pH 8.0 with 5N NaOH). PTH or the PTH variant, adsorbed to the column, was then eluted using as eluant a concentration gradient of buffer to 0.6M ammonium acetate (pH8.0).

Fractions containing PTH activity (as measured by Allegro two-site IRMA or monitored by $A_{280}$) were combined and then desalted by passage through a cartridge containing reversed phase C-18 resin e.g. Sep-Pak (Waters Inc.) or Amberchrom CG71 resin (Toso Haas) pre-equilibrated with 0.1% TFA. PTH or the PTH variant bound to the resin was eluted with 0. 1% TFA/80% acetonitrile. The desalted preparations were then frozen in liquid nitrogen, lyophilized and stored at −20° C.

Thawed or fresh samples of human PTH(1–84) and of PTH variants obtained as described above were then evaluated for biological activity in a UMR-106 based adenylate cyclase assay and the protocol as described by Rabbini et al, 1988, Endocrinology, 123:2709, which is incorporated herein by reference. As noted, rat osteosarcoma cells of the UMR line are stimulated by PTH to produce adenylate cyclase, an enzyme which catalyzes intracellular conversion of ATP to its cylic monophosphate analogue, cAMP. In this assay therefore, PTH activity is determined by assaying radiometrically the formation of cAMP in PTH-stimulated UMR cells. The results of the assays, expressed in terms of $EC_{50}$ (concentration of PTH or variant effective for half-maximal stimulation of adenylate cyclase activity), are presented in Table 1.

TABLE 1

Relative activities of PTH variants

| PTH variant | $EC_{50}$ (nM) |
|---|---|
| human PTH | 2 |
| [$Val^8Leu^{18}$] | 110 |
| [$Cys^8Leu^{18}$] | 200 |
| [$Cys^8$] | 400 |
| [$Ala^8$] | 1200 |
| [$Lys^8Leu^{18}$] | >5000 |
| [$Gln^8Leu^{18}$] | " |
| [$Asp^8Leu^{18}$] | " |
| [$Glu^8Leu^{18}$] | " |
| [$Arg^8Leu^{18}$] | " |

In reference to Table 1, it will be noted that bone stimulating activity similar to human PTH is retained by the each of the human PTH variants of the present invention. Also presented, for comparison, are bone stimulating activities of structurally related human PTH variants, to illustrate the relatively significant reduction in bone stimulating activity resulting from Met8 replacement amino acids other than Val, Cys and Ala.

Example 7—Analysis of Vasoactivity

The vaosrelaxant activity of the recombinant human PTH(1–84) and of the PTH variants was also assessed in two cariovascular assays, one measuring changes in blood pressure in anaesthetized rats receiving the particular compound in a normal saline vehicle by tail vein injection at the doses noted in FIG. 3A and another measuring compound-induced effects on relaxation of AVP($3\times10^{-9}$M)contracted helical strips taken from rat tail vein, performed as described by Daugirdas et al, supra (FIG. 3B).

In reference to FIGS. 3A and 3B, it will be noted that each of the compounds exhibited virtually no vasorelaxant activity relative to PTH, in both the blood pressure and helical strip assays. Taken together, these results demonstrate that the vasorelaxant activity exhibited by mammalian PTH is markedly, reduced and the bone stimulating activity substantially retained, when the $Met^8$ resident therein is replaced by one of Cys, Ala and Val. This same beneficial activity profile is retained by variants of these compounds in which $Met^{18}$ is replaced, for example by leucine.

We claim:

1. A bone-stimulating compound having reduced vasorelaxant activity as compared to natural human parathyroid hormone (hPTH) selected from the group consisting of [$Cys^8$]hPTH (1–84), [$Ala^8$]hPTH (1–84), and [$Cys^8Leu^{18}$] hPTH (1–84).

2. A bone-stimulating compound having reduced vasorelaxant activity as compared to natural hPTH as defined in claim 1, wherein said compound is [$Cys^8$]hPTH(1–84).

3. A bone-stimulating compound having reduced vasorelaxant activity as compared to natural hPTH as defined in claim 1, wherein said compound is [$Ala^8$]hPTH(1–84).

4. A bone-stimulating compound having reduced vasorelaxant activity as compared to natural hPTH as defined in claim 1, wherein said compound is [$Cys^8Leu^{18}$] hPTH(1–84).

5. A pharmaceutical composition comprising a pharmaceutically acceptable carrier and a compound as claimed in claim 1.

6. A pharmaceutical composition according to claim 5, wherein the compound is [$Cys^8$]hPTH(1–84).

7. A pharmaceutical composition according to claim 5, wherein the compound is [$Ala^8$]hPTH(1–84).

8. A pharmaceutical composition according to claim 5, wherein the compound is [$Cys^8Leu^{18}$]hpTH(1–84).

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 252 base pairs
        ( B ) TYPE: nucleic acid
        ( C ) STRANDEDNESS: double
        ( D ) TOPOLOGY: linear ( v i ) ORIGINAL SOURCE:
        ( A ) ORGANISM: hPTH ( i x ) FEATURE:
        ( A ) NAME/KEY: CDS
        ( B ) LOCATION: 1..252

( x i ) SEQUENCE DESCRIPTION: SEQ ID NO:1:

```
TCT  GTG  AGT  GAA  ATA  CAG  CTT  ATG  CAT  AAC  CTG  GGA  AAA  CAT  CTG  AAC      4 8
Ser  Val  Ser  Glu  Ile  Gln  Leu  Met  His  Asn  Leu  Gly  Lys  His  Leu  Asn
 1                 5                          10                      15

TCG  ATG  GAG  AGA  GTA  GAA  TGG  CTG  CGT  AAG  AAG  CTG  CAG  GAT  GTG  CAC      9 6
Ser  Met  Glu  Arg  Val  Glu  Trp  Leu  Arg  Lys  Lys  Leu  Gln  Asp  Val  His
             20                     25                          30

AAT  TTT  GTT  GCC  CTT  GGA  GCT  CCT  CTA  GCT  CCC  AGA  GAT  GCT  GGT  TCC      144
Asn  Phe  Val  Ala  Leu  Gly  Ala  Pro  Leu  Ala  Pro  Arg  Asp  Ala  Gly  Ser
         35                         40                      45

CAG  AGG  CCC  CGA  AAA  AAG  GAA  GAC  AAT  GTC  TTG  GTT  GAG  AGC  CAT  GAA      192
Gln  Arg  Pro  Arg  Lys  Lys  Glu  Asp  Asn  Val  Leu  Val  Glu  Ser  His  Glu
```

```
                    50                         55                        60
AAA  AGT  CTT  GGA  GAG  GCA  GAC  AAA  GCT  GAT  GTG  AAT  GTA  TTA  ACT  AAA        240
Lys  Ser  Leu  Gly  Glu  Ala  Asp  Lys  Ala  Asp  Val  Asn  Val  Leu  Thr  Lys
65                       70                       75                       80

GCT  AAA  TCC  CAG                                                                     252
Ala  Lys  Ser  Gln
```

( 2 ) INFORMATION FOR SEQ ID NO:2:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ser  Val  Ser  Glu  Ile  Gln  Leu  Met  His  Asn  Leu  Gly  Lys  His  Leu  Asn
1                     5                    10                       15

Ser  Met  Glu  Arg  Val  Glu  Trp  Leu  Arg  Lys  Lys  Leu  Gln  Asp  Val  His
               20                        25                       30

Asn  Phe  Val  Ala  Leu  Gly  Ala  Pro  Leu  Ala  Pro  Arg  Asp  Ala  Gly  Ser
          35                        40                       45

Gln  Arg  Pro  Arg  Lys  Lys  Glu  Asp  Asn  Val  Leu  Val  Glu  Ser  His  Glu
     50                        55                       60

Lys  Ser  Leu  Gly  Glu  Ala  Asp  Lys  Ala  Asp  Val  Asn  Val  Leu  Thr  Lys
65                       70                       75                       80

Ala  Lys  Ser  Gln
```

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CTCTCTCCAG CGAGTTC                                                                     17

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCAGGTTATG AACAAGCTGT ATTTCAC                                                          27

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CCAGGTTATG AGCAAGCTGT ATTTCAC                                                          27

( 2 ) INFORMATION FOR SEQ ID NO:6:

(  i  ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

CCAGGTTATG GCAAAGCTGT ATTTCAC      27